(12) United States Patent
Watanabe et al.

(10) Patent No.: US 7,911,599 B2
(45) Date of Patent: Mar. 22, 2011

(54) RETICLE DEFECT INSPECTION APPARATUS AND RETICLE DEFECT INSPECTION METHOD

(75) Inventors: Toshiyuki Watanabe, Kanagawa (JP); Riki Ogawa, Kanagawa (JP)

(73) Assignees: Kabushiki Kaisha Toshiba, Tokyo (JP); NEC Corporation, Tokyo (JP)

( * ) Notice: Subject to any disclaimer, the term of this patent is extended or adjusted under 35 U.S.C. 154(b) by 401 days.

(21) Appl. No.: 12/047,554

(22) Filed: Mar. 13, 2008

(65) Prior Publication Data

US 2008/0239290 A1      Oct. 2, 2008

(30) Foreign Application Priority Data

Mar. 30, 2007   (JP) .................................. 2007-090054

(51) Int. Cl.
*G01N 21/00* (2006.01)
*G01N 21/88* (2006.01)
(52) U.S. Cl. .................................. 356/237.5; 356/237.4
(58) Field of Classification Search ..... 356/237.1–237.6
See application file for complete search history.

(56) References Cited

U.S. PATENT DOCUMENTS

| | | | |
|---|---|---|---|
| 5,563,702 A | 10/1996 | Emery et al. | |
| 5,572,598 A | 11/1996 | Wihl et al. | |
| 6,268,093 B1 * | 7/2001 | Kenan et al. | 430/30 |
| 6,466,315 B1 * | 10/2002 | Karpol et al. | 356/237.4 |
| 6,909,501 B2 * | 6/2005 | Ogawa et al. | 356/237.5 |
| 7,065,240 B2 * | 6/2006 | Tada | 382/145 |
| 7,068,364 B2 * | 6/2006 | Sugihara et al. | 356/237.5 |
| 7,126,681 B1 * | 10/2006 | Chen et al. | 356/237.4 |
| 7,304,730 B2 * | 12/2007 | Inoue et al. | 356/237.1 |
| 7,345,755 B2 * | 3/2008 | Ogawa et al. | 356/237.5 |
| 7,372,560 B2 * | 5/2008 | Tojo et al. | 356/237.5 |
| 7,508,526 B2 * | 3/2009 | Ogawa et al. | 356/491 |

FOREIGN PATENT DOCUMENTS

| | | |
|---|---|---|
| AO | 4-318550 | 11/1992 |
| JP | 10-97053 | 4/1998 |
| JP | 11-83753 | 3/1999 |
| JP | 11-311608 | 11/1999 |
| JP | 2004-70249 | 3/2004 |
| JP | 2004-301751 | 10/2004 |
| JP | 2005-266622 | 9/2005 |

OTHER PUBLICATIONS

Toru Tojo, et al., "Mask Defect Inspection Method by Database Comparison with 0.25-0.35 μm Sensitivity", Jpn. J. Appl. Phys., vol. 33, Part 1, No. 12B, Dec. 1994, pp. 7156-7162.

(Continued)

*Primary Examiner* — Sang Nguyen
(74) *Attorney, Agent, or Firm* — Oblon, Spivak, McClelland, Maier & Neustadt, L.L.P.

(57) ABSTRACT

A reticle defect inspection apparatus that can carry out a defect inspection with high detection sensitivity are provided. The apparatus includes an optical system of transmitted illumination for irradiating one surface of a sample with a first inspection light, an optical system of reflected illumination for irradiating another surface of the sample with a second inspection light, and a detecting optical system that can simultaneously detect a transmitted light obtained by the first inspection light being passed through the sample and a reflected light obtained by the second inspection light being reflected by the sample. And the optical system of transmitted illumination includes a focusing lens driving mechanism for correcting a focal point shift of the transmitted light resulting from thickness of the sample.

4 Claims, 7 Drawing Sheets

OTHER PUBLICATIONS

Yasutaka Morikawa, et al., "Performance of cell-shift defect inspection technique", Photomask and X-Ray Mask Technology IV, vol. 3096, 1997, pp. 404-414.

Office Action issued Oct. 26, 2010, in Japanese Patent Application No. 2007-090054 (with English-language Translation).

* cited by examiner

SCAN WIDTH W

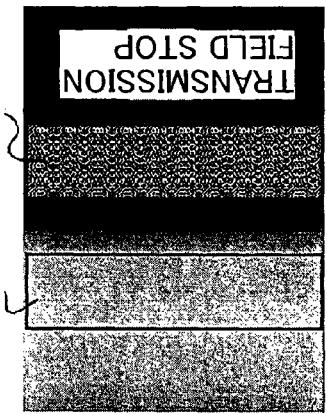 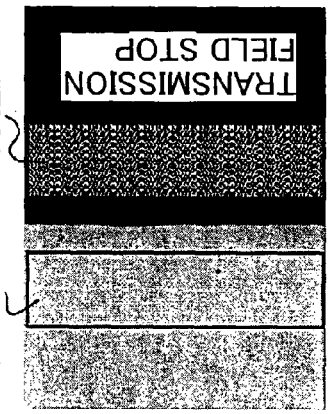 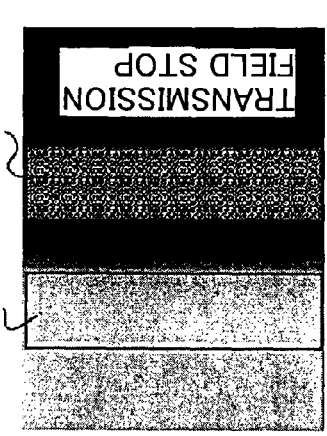
FIG.4A — − DEFOCUSING (CORRESPONDING TO RETICLE THICKNESS −0.1 mm)
FIG.4B — ILLUMINATION SYSTEM FOCUSED POSITION
FIG.4C — + DEFOCUSING (CORRESPONDING TO RETICLE THICKNESS +0.1 mm)
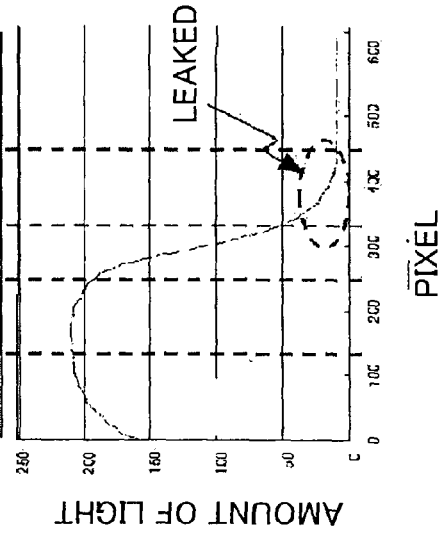 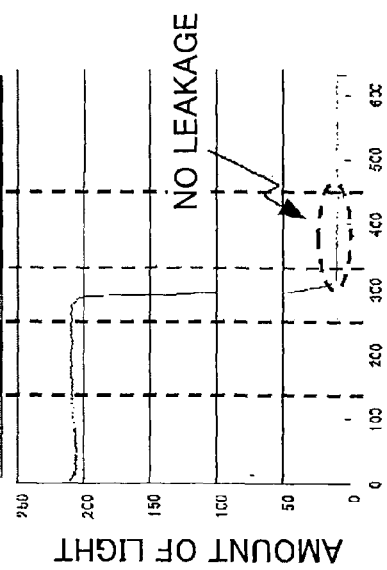 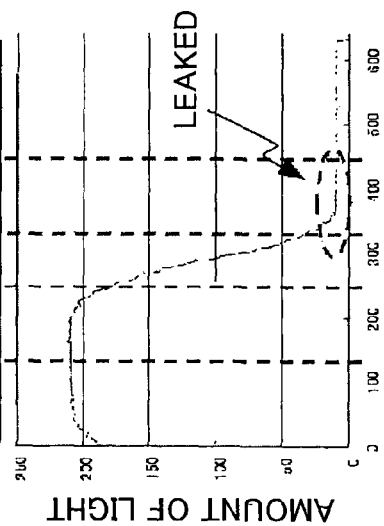

RETICLE DEFECT INSPECTION APPARATUS AND RETICLE DEFECT INSPECTION METHOD

CROSS-REFERENCE TO RELATED APPLICATION

This application is based upon and claims the benefit of priority from Japanese Patent Application No. 2007-090054, filed on Mar. 30, 2007, the entire contents of which are incorporated herein by reference.

FIELD OF THE INVENTION

The present invention relates to a reticle defect inspection apparatus and a reticle defect inspection method using a transmitted light and a reflected light for inspection.

BACKGROUND OF THE INVENTION

Patterns constituting a large-scale integrated circuit (LSI), as exemplified by DRAM of a gigabit class, have a minimum feature size on the order of submicron to nanometer. One of major causes for yield reduction in a manufacturing process of such an LSI includes defects on a reticle (also called a mask) used when a fine pattern is exposed and formed onto a semiconductor wafer using lithography technology.

Particularly with increasingly finer pattern dimensions of LSI formed on a semiconductor wafer, dimensions that must be detected as pattern defects are also becoming extremely smaller. Thus, apparatuses for inspecting for extremely small defects are vigorously being developed.

With progression of multimedia, on the other hand, an LCD is getting increasingly larger with a liquid crystal substrate size of 500 mm×600 mm or more and a pattern such as a thin-film transistor (TFT) formed on the liquid crystal is becoming increasingly finer, demanding an extensive inspection of extremely small pattern defects. Thus, development of an inspection apparatus for efficiently inspecting for defects of a reticle (photomask) used for manufacture of a large-area LCD in a short time is also urgently necessary.

Mainly a transmitting optical system is used as an optical system of a defect inspection apparatus of reticle and the like. That is, a sample surface is shone using Koehler illumination as shown in FIG. 5A or critical illumination as shown in FIG. 5B and then, a transmitted light thereof is condensed and led to a detection system before image data is extracted. A defect inspection apparatus of a method using a transmitted light is introduced, for example, in JJPA, Vol. 33 (1994), pp 7156-71-62, "Mask defect inspection method by database comparison with 0.25-0.35 μm sensitivity".

In recent years, however, attempts to inspect for defects that are difficult to detect by a transmitted light by using a reflected image have been made. For example, a pattern (defect) inspection apparatus that tries to improve detection sensitivity by using an optical system as shown in FIG. 6 and mounting a transmitted/reflected light optical system is already in practical use (for example, Photomask and X-Ray Mask Technology IV, Vol. 3096 (1997), pp 404-414, "Performance of cell-shift defect inspection technique"). In such an apparatus, two wavelengths, one ($\lambda 2$ in FIG. 6) used for transmitted light inspection and one ($\lambda 1$ in FIG. 6) used for reflected light inspection, are separated by a filter inside a configured optical system based on wavelengths and each light is brought into a transmission sensor or a reflection sensor for detection.

Indeed, it has become necessary to make the wavelengths shorter to improve defect detection sensitivity. Further, making inspection wavelengths shorter has become necessary all the more because inspected matter increasingly requires inspection at wavelengths adjusting to those used for lithography in order to improve detection sensibility. On the other hand, making inspection wavelengths shorter makes design of an optical lens more difficult, particularly design of a lens whose aberration is made smaller for both two wavelengths. Thus, a problem arises that it is difficult for a detection apparatus that detects defects of the size of 10 nm or so to adopt an optical system in which a different wavelength is used for transmission and reflection. Therefore, the necessity of an inspection method that acquires transmission and reflection images using a single wavelength arises.

Here, when an observation is made using a transmitted light and a reflected light of a single wavelength, a method by which the same position is coaxially shone to gather observation images has generally been used (for example, U.S. Pat. Nos. 5,572,598; 5,563,702). In this method, a beam scan technology is generally adopted. FIG. 7 shows a beam scan type optical system. Since resolution can be increased for the beam scan type as beam spots formed on a reticle pattern surface become smaller, an illuminating optical system is produced by pursuing an aberration to the limit. And an inspection light is introduced from a patterned surface of a reticle to avoid an influence of thickness of the reticle. On the other hand, a light transmitted through or reflected by a reticle only needs to enter a photodiode or photomultiplier because it is necessary only to measure the amount of light. Therefore, an optical system receiving light need not pursue an aberration and thus, no particular problem arises even if measurement is made on the glass surface side.

Indeed, when realizing a simultaneous inspection of transmission and reflection in a projecting optical system in which a reticle image is formed on a sensor, in contrast to the beam scan type, resolution is determined by performance of an image-forming optical system after being transmitted through or reflected by a reticle. Here, the image-forming optical system must be arranged on the side of the pattern surface of a reticle so that the image-forming optical system is not affected by the glass thickness of a reticle. Therefore, a transmitted illumination light must be introduced from the glass surface side of a reticle and a reflected illumination light from the pattern surface side of the reticle.

To realize a simultaneous inspection of transmission and reflection in a projecting optical system under such conditions, two optical systems shown in FIG. 8 and FIG. 9 can be considered. In a method shown in FIG. 8, directions of polarized lights incident on the reticle surface after transmission and reflection are caused to be perpendicular to each other, and a light ray transmitted through the reticle and a light reflected by the reticle are separated by a polarization beam splitter. This method has an advantage of being able to image the same position on the reticle simultaneously, but due to separation of polarized light, both lights mix together to the extent that the polarized lights are disturbed by reflection by optical elements or reticle surface or the like, leading to a lower contrast. Therefore, this method may cause a problem in a reticle defect inspection apparatus that requires high-precision inspection. A method shown in FIG. 9, on the other hand, is a method by which a transmitted illumination area and a reflected illumination area are positionally separated (for example, JP-A 2004-301751(KOKAI)). By separating both areas, a transmitted light and a reflected light can be prevented from being mixed together.

SUMMARY OF THE INVENTION

Since a transmitted illumination light is incident on a reticle pattern surface after passing through a glass, a focal point shift depending on reticle thickness arises. Though no focal point shift arises if the reticle thickness is constant, thickness of reticle actually used varies within a tolerance (for example, ±0.1 mm) and thus, it is necessary to focus transmitted illumination for each reticle. While, if a transmitted illumination area and a reflected illumination area should positionally be separated, settings must be made so that the transmitted illumination area and the reflected illumination area do not overlap, it has become evident that a problem arises in which blurring of illuminated areas occurs due to the focal point shift before being expanded so that the transmitted illumination light penetrates into a reflected imaging area. Such problems must be tackled in order to carry out a defect inspection with high detection sensibility by simultaneous inspection of transmission and reflection.

A reticle defect inspection apparatus in accordance with an aspect of the present invention is a reticle defect inspection apparatus for inspecting for defects on a measured sample using a pattern image obtained by irradiating the sample on which patterns are formed with light that comprises: an optical system of transmitted illumination for irradiating one surface of the sample with a first inspection light; a reflected illumination optical system for irradiating another surface of the sample with a second inspection light; and a detecting optical system that can simultaneously detect a transmitted light obtained by the first inspection light being transmitted through the sample and a reflected light obtained by the second inspection light being reflected by the sample, wherein the optical system of transmitted illumination comprises a focusing lens driving mechanism for correcting a focal point shift of the transmitted light resulting from thickness of the sample.

A reticle defect inspection method in accordance with an aspect of the present invention is a reticle defect inspection method for inspecting for defects on a sample using a pattern image obtained by irradiating the sample on which patterns are formed with light, wherein a reference pattern is imaged using an inspection light shone on the sample from an optical system of transmitted illumination and a reference pattern image obtained by imaging the reference pattern is focused by driving a focusing lens driving mechanism.

BRIEF DESCRIPTION OF THE DRAWINGS

FIG. 4 is a diagram showing images and light quantity distributions of a transmission field stop in the embodiment.

DETAILED DESCRIPTION OF THE EMBODIMENTS

An embodiment of the present invention will be described below with reference to drawings. A reticle defect inspection apparatus in the present embodiment is a reticle defect inspection apparatus that inspects for defects on a sample by using a pattern image obtained by irradiating the sample on which a pattern is formed with light. The reticle defect inspection apparatus comprises an optical system of transmitted illumination that irradiates one surface of the sample with a first inspection light and an optical system of reflected illumination that irradiates another surface of the sample with a second inspection light. Moreover, the reticle defect inspection apparatus comprises a detecting optical system that can detect a transmitted light by irradiation of the sample with the first inspection light and a reflected light by irradiation of the sample with the second inspection light simultaneously. Further, the optical system of transmitted illumination comprises a lens driving mechanism for focal point correction that corrects a focal point shift of a transmitted light caused by thickness of the sample.

Figure 2:
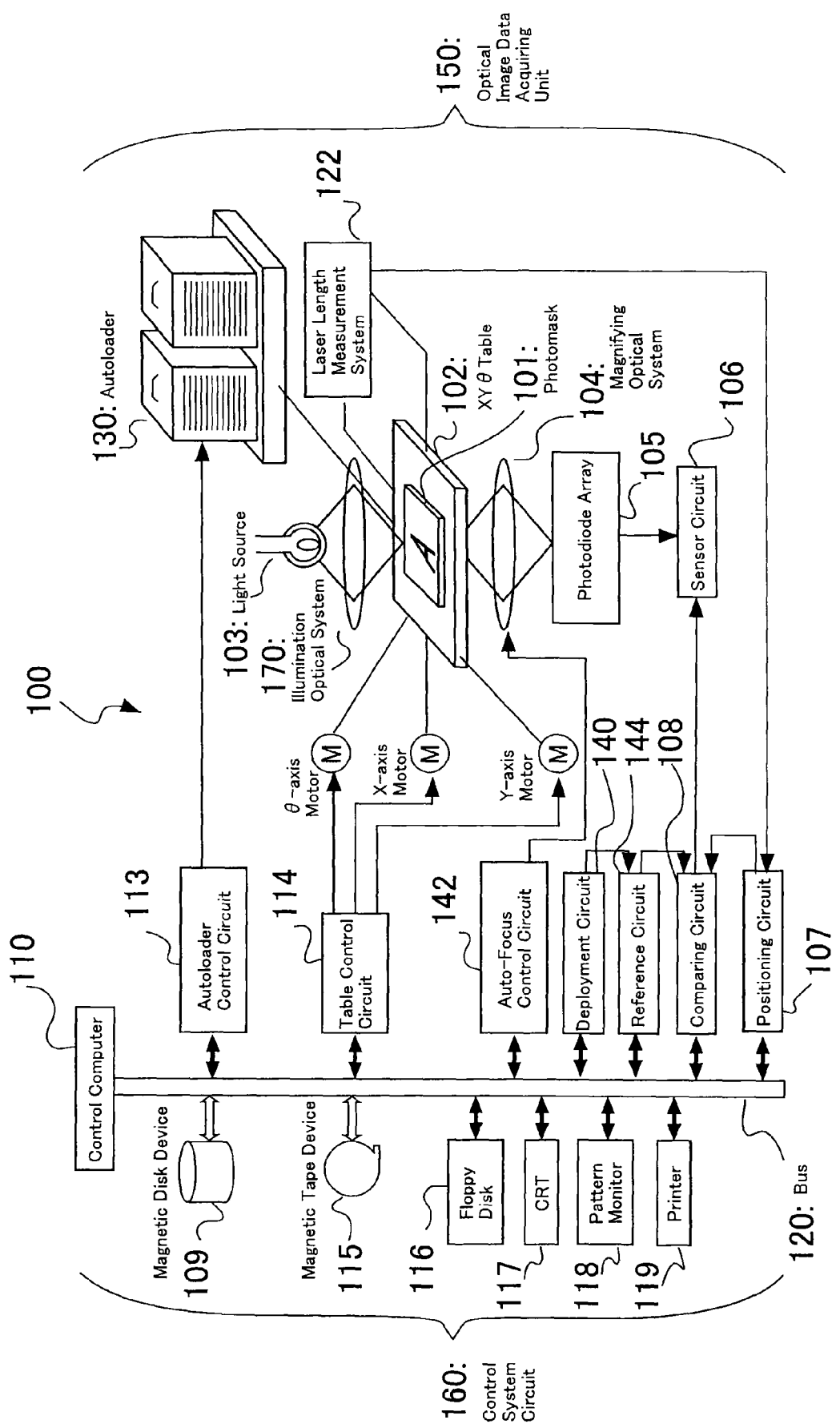
FIG. 2 is a diagram showing an overall configuration of the reticle defect inspection apparatus in the embodiment.
Figure 3:
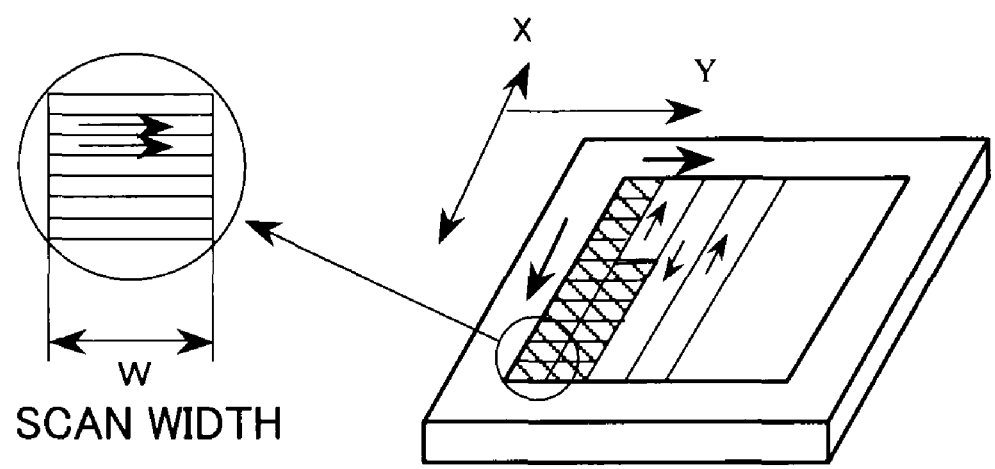
FIG. 3 is an explanatory view of inspection stripes of an inspected area in the embodiment.
Figure 5A:
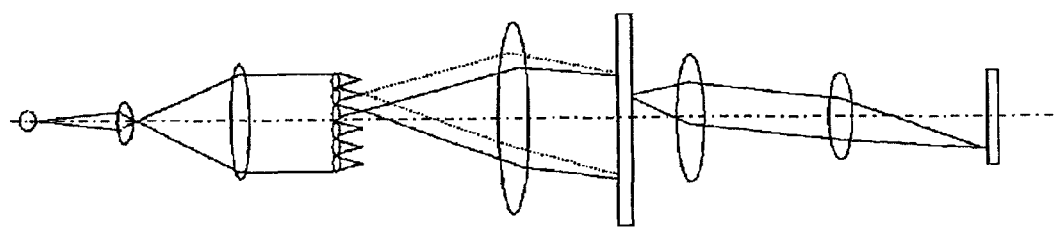
FIG. 5 is an explanatory view of a transmission type optical system of a conventional defect inspection apparatus.
Figure 5B:
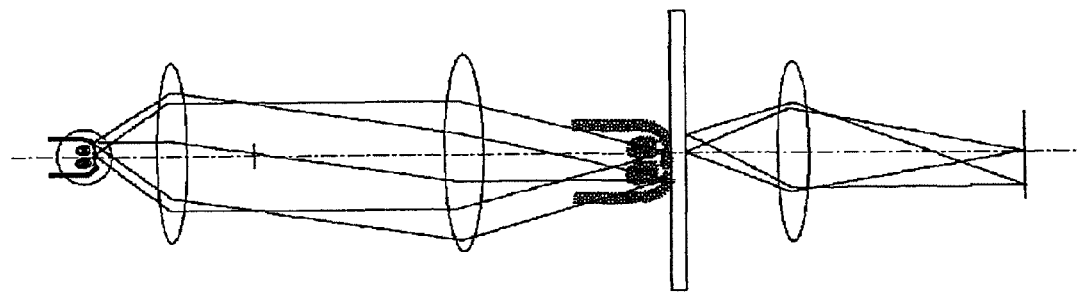
Figure 6:
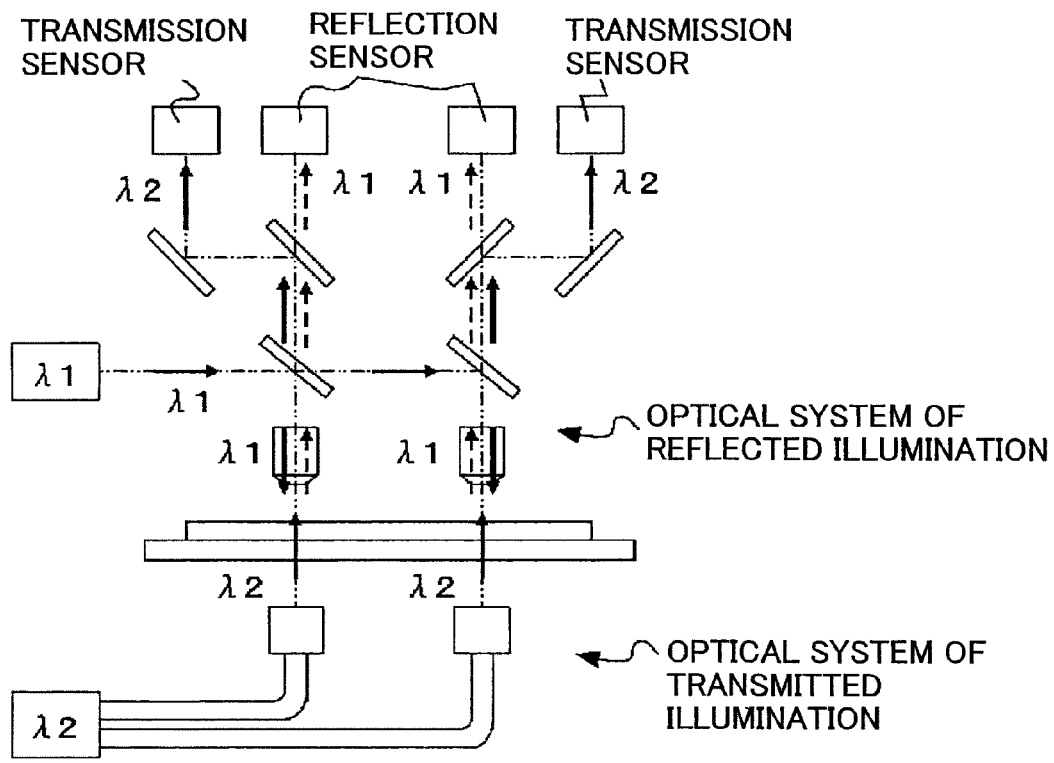
FIG. 6 is an explanatory view of the conventional defect inspection apparatus.
Figure 7:
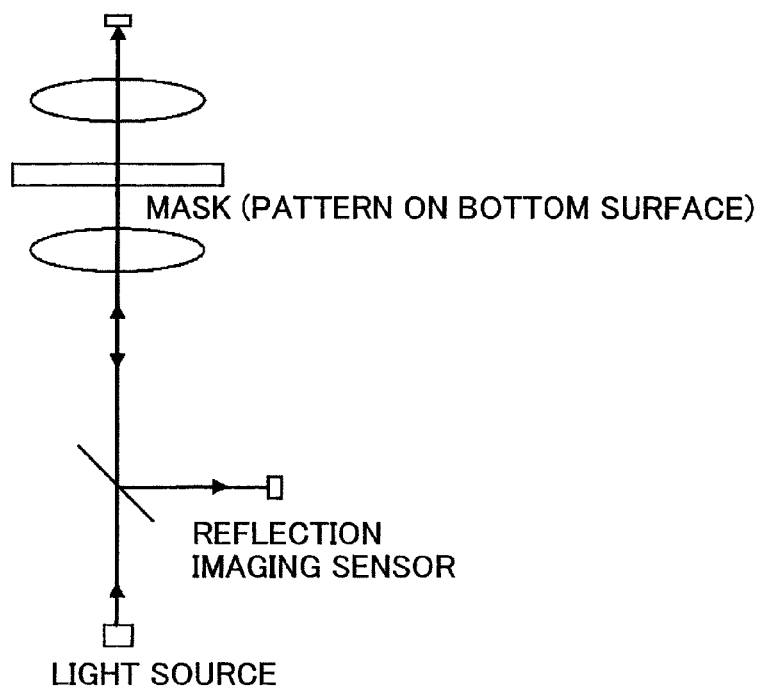
FIG. 7 is a diagram showing a conventional beam scan type optical system.
Figure 8:
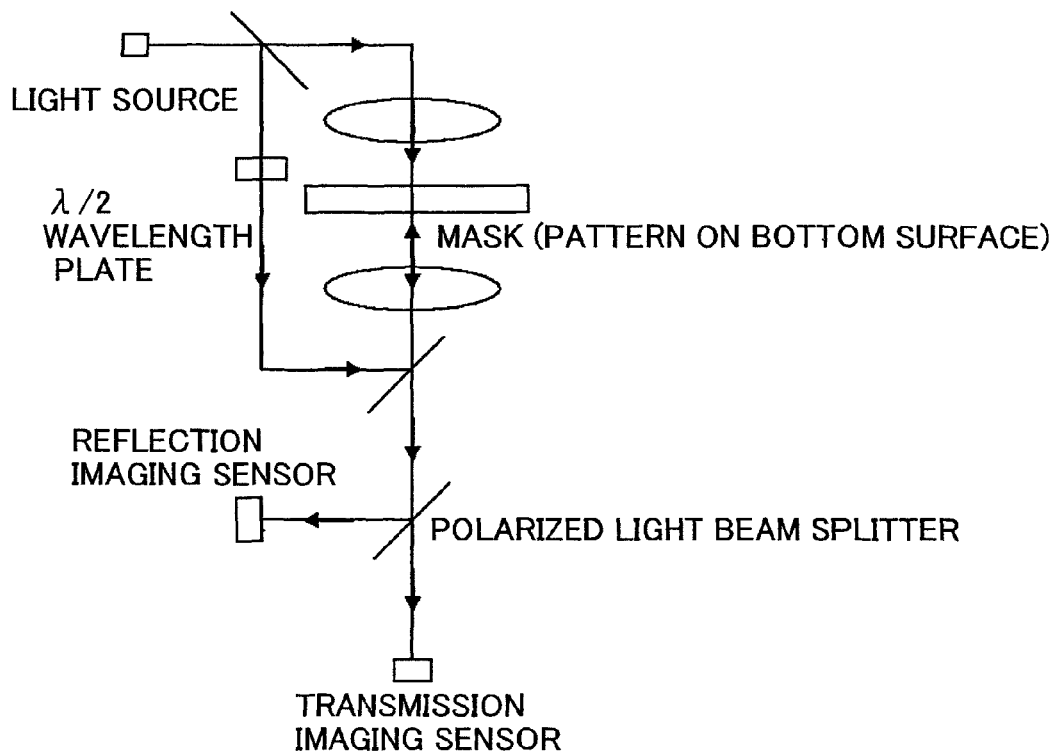
FIG. 8 is a diagram showing a conventional projecting optical system.
Figure 9:
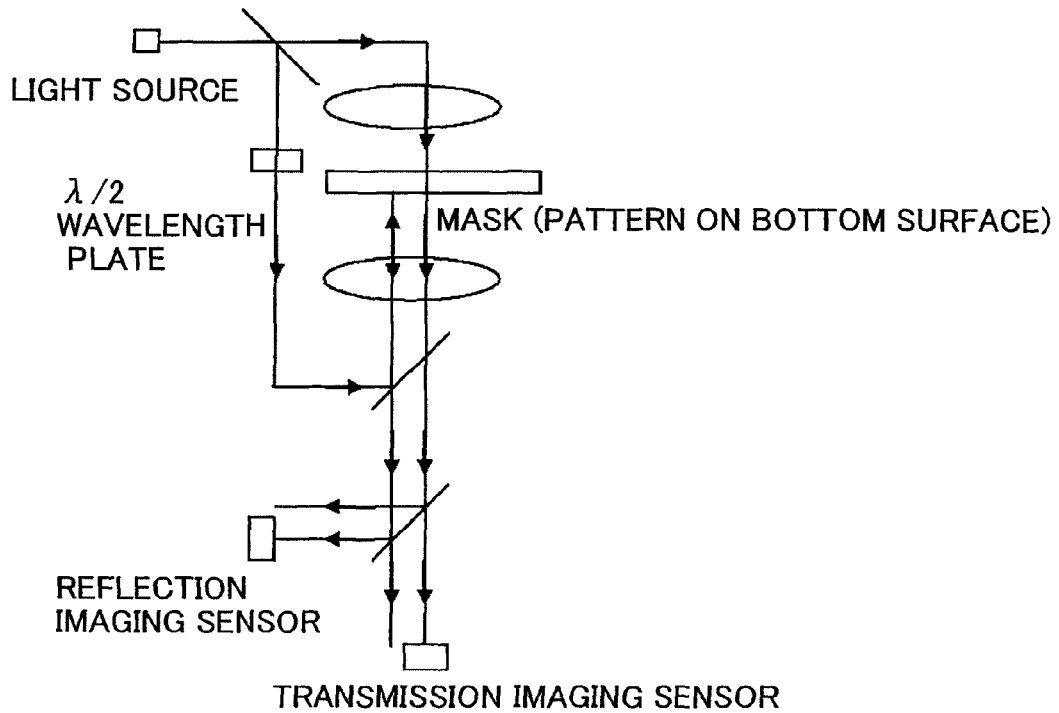
FIG. 9 is a diagram showing a conventional projecting optical system.

FIG. 2 is a diagram showing an overall configuration of the reticle defect inspection apparatus in the present embodiment. In a reticle defect inspection apparatus 100 shown in FIG. 2, an inspected area in a pattern formed on a reticle (or a photomask) 101, which is a sample to be evaluated, is virtually divided, as shown in FIG. 3, into inspection stripes in a strip shape having a width W. An inspection is carried out by putting the reticle 101 on an XYθ table 102 shown in FIG. 2 and continuously moving a uniaxial stage so that the divided inspection stripes are continuously operated. When an inspection of one stripe is completed, step movement occurs for observation of the next stripe.

The reticle 101 is put on the XYθ table 102 using an autoloader 130 and an autoloader control circuit 113, but a pattern may not always be in parallel with a running axis of the table. Thus, the reticle 101 is in most cases fixed onto a rotatable θ stage so that the reticle 101 can be mounted in parallel with the running axis. The above XYθ table 102 is controlled by using an X-axis motor, a Y-axis motor, a θ-axis motor, and a table control circuit 114.

A pattern formed on the reticle 101 is irradiated by an illumination optical system 170 with a light emitted from a suitable light source 103. After passing through the reticle, the light is incident on a photodiode array 105, which is an imaging device for inspection, via an magnifying optical system 104. A portion of a strip-shaped area of the virtually divided pattern shown in FIG. 3 is magnified on the photodiode array 105 before being formed as an optical image. The magnifying optical system 104 is autofocus-controlled in order to maintain good image-forming conditions.

A pattern image formed on the photodiode array 105 undergoes a photoelectric conversion by the photodiode array 105 and further an A/D conversion by a sensor circuit 106. Measured image data output from the sensor circuit 106 is sent to a comparing circuit 108 together with data indicating the position of the reticle 101 on the XYθ table 102 output from a positioning circuit 107.

Design data used for pattern formation of the reticle 101, on the other hand, is read from a magnetic disk device 109 to a deployment circuit 140 via a control computer 110. The read design data is converted by the deployment circuit 140 into two-valued or multi-valued design image data, which is sent to a reference circuit 144. The reference circuit 144 performs suitable filter processing on the sent graphic design image data.

The filter processing is performed because a filter has acted on measured pattern data acquired from the sensor circuit 106 by resolution characteristics of the magnifying optical system 104, an aperture effect of the photodiode array 105 or the like and thus, the filter processing is performed also on the design image data to adjust the design image data to the measured image data. The comparing circuit 108 compares the measured image data with the design image data on which suitable filter processing has been performed according to an appropriate algorithm and, if both pieces of data do not match, determines that the reticle is defective.

In a reticle inspection apparatus in the present embodiment for inspecting for defects or foreign matter existing in a pattern formed on the surface of a reticle, which is an inspected sample, a reticle pattern image is formed using an optical system similar to a high-resolution microscope, the reticle pattern image is acquired as image information using, for example, a CCD camera like the aforementioned photodiode array or an imaging device such as a line sensor, and the image information is compared with a reference image acquired or formed separately to detect defects or foreign matter in the pattern.

Incidentally, a detailed configuration of the optical system of transmitted illumination, optical system of reflected illumination, and detecting optical system to realize a simultaneous inspection of transmission and reflection is not shown in FIG. 2. For realization of a simultaneous inspection of transmission and reflection, it is necessary to provide an optical system of transmitted illumination, an optical system of reflected illumination, and a corresponding detecting optical system, and further two systems of the comparing circuit 108 or the like for defect detection.

Figure 1:
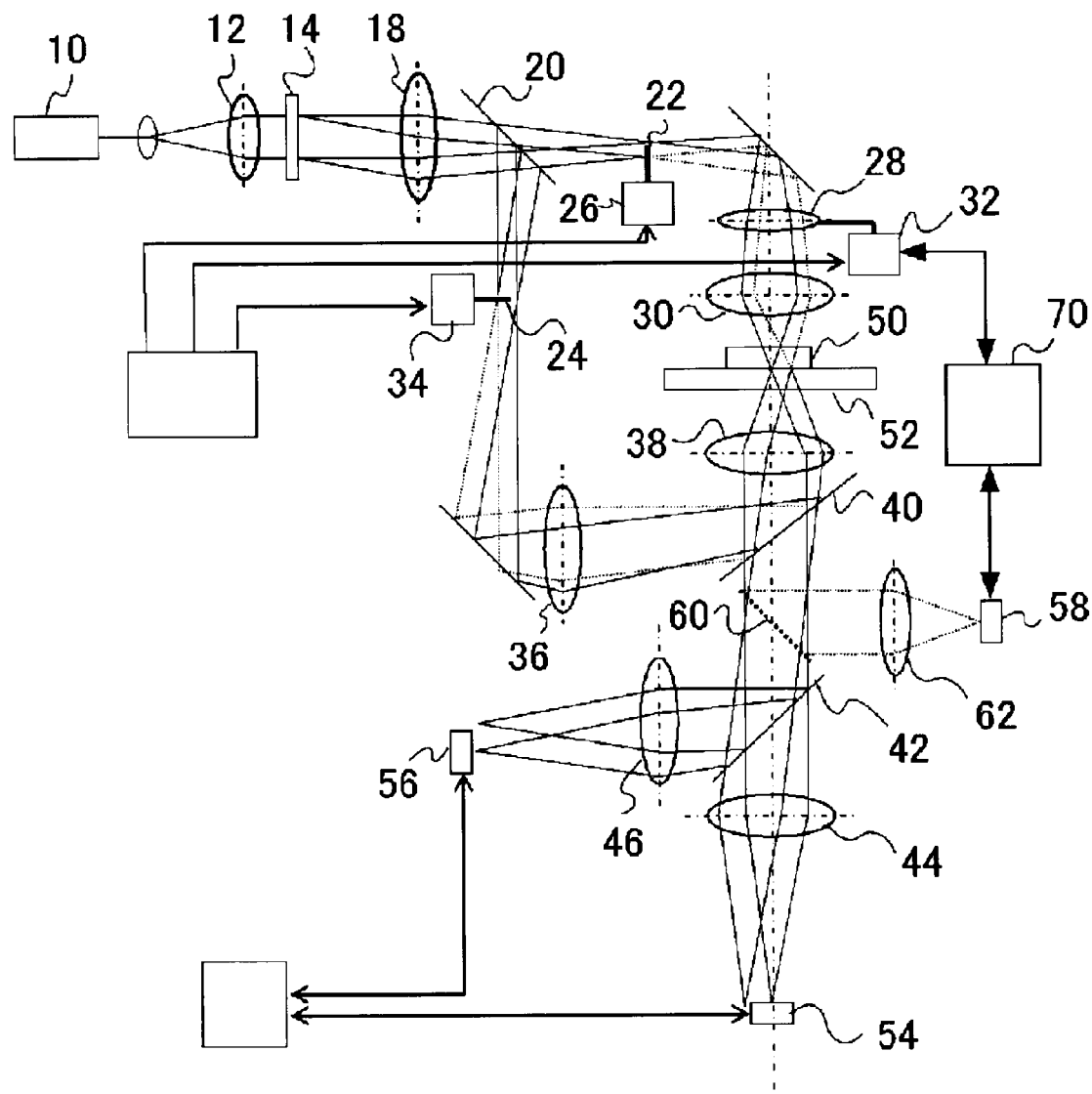
FIG. 1 is a diagram showing an optical system of a reticle defect inspection apparatus in an embodiment.

FIG. 1 is a diagram showing an optical system of the reticle defect inspection apparatus in the present embodiment. Of the overall configuration diagram shown in FIG. 2, a portion corresponding to the light source 103, the illuminating optical system 170, the reticle 101, the XYθ table 102, the magnifying optical system 104, the photodiode array 105, and the sensor circuit 106 is shown.

First, the optical system in FIG. 1 comprises a light source 10. The optical system also comprises a beam expander 12 for expanding a light emitted from the light source 10 and an optical integrator 14 for making the light a surface light source. More specifically, a fly eye lens or a diffuser panel can be used as the optical integrator 14.

Moreover, the optical system comprises a collimator 18 for making a light that passes through the optical integrator 14 parallel rays. A first beam splitter 20 has a function of splitting parallel rays that have passed through the collimator 18 into a transmitted illumination light, which is a first inspection light, and a reflected illumination light, which is a second inspection light. Here, an optical system from the first beam splitter 20 up to reticle 50 which irradiated with the transmitted illumination light, which is the first inspection light, is called an optical system of transmitted illumination. An optical system up to the reticle 50 which irradiated with the reflected illumination light, which is the second inspection light, is called an optical system of reflected illumination.

The optical system of transmitted illumination and the optical system of reflected illumination are each configured so that the transmitted illumination light and the reflected illumination light are provided as Koehler illumination at positions of a transmission field stop 22 and a reflection field stop 24 respectively. In this specification, "a transmission field stop" means a field stop in the optical system of transmitted illumination and "a reflection field stop" means a field stop in the optical system of reflected illumination. The position of the transmission field stop 22 is set in such a way that the position and a pattern surface of the reticle 50 are conjugate and an area regulated and illuminated by the transmission field stop 22 becomes a transmitted illumination area. A first pulse motor 26 for driving the transmission field stop 22 is also provided to set a viewing position. Moreover, a focusing lens 28 and a condenser lens 30 are also arranged so that a light, after passing through the transmission field stop 22, is provided as Koehler illumination on the pattern surface of the reticle 50. Incidentally, the focusing lens here may be a dedicated focusing lens or a lens constituting a portion of the condenser lens 30.

Further, the optical system of transmitted illumination has a second pulse motor 32, which is a focusing lens driving mechanism, to correct a focal point shift of a transmitted light caused by thickness of the reticle 50. The second pulse motor 32 causes parallel movement of the focusing lens 28 in a direction of optical axis so that the focus can be adjusted to the pattern surface at the bottom of the reticle 50 in FIG. 1.

The position of the reflection field stop 24, on the other hand, is set in such a way that the position and the pattern surface of the reticle 50 are conjugate and an area regulated and illuminated by the reflection field stop 24 becomes a reflected illumination area. A third pulse motor 34 for driving the reflection field stop 24 is also provided to set a viewing position. Moreover, a collimator 36 and an objective lens 38 are also arranged so that a light, after passing through the reflection field stop 24, is provided as Koehler illumination on the pattern surface of the reticle 50. A second beam splitter 40 is provided between the collimator 36 and the objective lens 38 to introduce a reflected illumination light onto the pattern surface.

In addition, the reticle defect inspection apparatus in the present invention has a detecting optical system that can simultaneously detect a transmitted light obtained by irradiation of the reticle 50 with the first inspection light and a reflected light obtained by irradiation of the sample with the second inspection light. First, the objective lens 38 for condensing both the transmitted light and reflected light is provided as a component of the detecting optical system. Further, a third beam splitter 42 for separating the light condensed by the objective lens 38 into a transmitted light and a reflected light is provided. Also, a first image-forming optical system 44 for forming an image of the transmitted light separated by the third beam splitter 42 and a second image-forming optical system 46 for forming an image of the reflected light separated by the third beam splitter 42 are provided.

Further, the reticle defect inspection apparatus in the present invention comprises a first imaging sensor 54, which is an imaging device for inspection of pattern images by the transmitted light whose image is formed by the first image-forming optical system 44, and a second imaging sensor 56, which is an imaging device for inspection of pattern images by the reflected light whose image is formed by the second image-forming optical system 46 are provided.

According to the reticle defect inspection apparatus in the present embodiment described above, even if a focal point shift of a transmitted light resulting from thickness of a reticle arises, the focal point shift can be corrected by driving a focusing lens driving mechanism.

Further, the reticle defect inspection apparatus in the present embodiment may have a reference pattern formed in the optical system of transmitted illumination and an imaging means for observation of the reference pattern, which is independent of imaging device for inspection of pattern images, in order to facilitate corrections when a focal point shift of a transmitted light resulting from thickness of the reticle arises. However, the reference pattern and the imaging device for observation are not required components.

Here, a suitable pattern for focal point shift correction may be newly provided as the reference pattern, but it is preferable that the transmission field stop 22 in FIG. 1 be used as the reference pattern in order not to increase the number of components of the apparatus.

Also, the apparatus has a third imaging sensor 58, which is an imaging device for observation for imaging a reference pattern. The third imaging sensor 58 is independent of the first imaging sensor 54 and the second imaging sensor 56. Further, a mirror 60 insertable by a pulse motor (not shown) or the like is provided on an optical path between the objective lens 38 and the third beam splitter 42. In addition, a third image-forming optical system 62 that enables the third imaging sensor 58 to pick up an image of the reference pattern caused to be formed from a light introduced by the mirror 60 is provided.

The reticle defect inspection apparatus in the present embodiment is provided, as described above, with the reference pattern formed in the optical system of transmitted illumination and the imaging device for observation for acquiring an image of the reference pattern that is difficult to acquire by the imaging device for inspection in view of an inspection image acquisition area. Accordingly, the optical system can be made simple without the need for a mechanism to move the reference pattern to the inspection image acquisition area.

Further, the reticle defect inspection apparatus in the present embodiment comprises a correcting mechanism for correcting a reference pattern image obtained by imaging the reference pattern formed in the optical system of transmitted illumination using a focusing lens driving mechanism in order to maximize the contrast of the image so that corrections when a focal point shift of a transmitted light arises resulting from thickness of a reticle. However, this correcting mechanism is not a required component in the present invention.

More specifically, a correcting mechanism 70 arranged as shown in FIG. 1 is constituted, for example, by an A/D conversion processing part and an arithmetic processing part. The A/D conversion processing part digitizes a reference pattern image picked up by the third imaging sensor 58. The arithmetic processing part calculates the focusing lens position where a contrast of a reference pattern image, that is, a differential value of the amount of light of a reference pattern image, become maximum. The arithmetic processing part outputs information of the focusing lens position to a focusing lens driving mechanism. A differential value of the amount of light can be calculated by both of predetermined software and hardware.

By using the aforementioned correcting mechanism, accuracy of focal point shift corrections and workability thereof are further improved because focal point corrections can be made automatically and uniquely.

The aforementioned correcting mechanism may be a correcting mechanism for correcting a focal point shift of a transmitted light using thickness information of a measured reticle. In that case, the correcting mechanism will have an input device of thickness information of a measured reticle such as an input keyboard and an arithmetic processing part that calculates an optimal focusing lens position from the thickness information and outputs information of the focusing lens position to the focusing lens driving mechanism. According to the correcting mechanism described above, there is an advantage that a time needed for corrections can further be reduced by making acquisition of a reference pattern image and processing such as contrast calculation unnecessary.

Next, a reticle defect inspection method using a reticle defect inspection apparatus in the present embodiment will be described with reference to FIG. 1. First, a reference pattern is imaged using an inspection light shone on the reticle 50, which is a sample to be evaluated, from an optical system of transmitted illumination. Here, the transmission field stop 22 in the optical system of transmitted illumination is used. As described above, the transmission field stop 22 is set as a position, which is conjugate with the pattern surface of the reticle 50. Then, the reference pattern is imaged by the third imaging sensor 58 after the mirror 60 being inserted between the objective lens 38 and the third beam splitter 42.

FIG. 4 shows images and light quantity distributions of the transmission field stop 22 actually picked up according to the above method. FIG. 4A shows a defocused image when a reticle is thinner by 0.1 mm, FIG. 4B shows an image when no focal point shift occurs, and FIG. 4C shows defocused image when a reticle is thicker by 0.1 mm. Areas enclosed by a solid line in the images of the figure are transmission fields, which are inspection areas by a transmitted light and hatched areas are reflection fields, which are inspection areas by a reflected light. A right half of each image is an area into which originally no light penetrates by being blocked by the transmission stop.

As is evident from the figure, when a focal point shift occurs due to a tolerance of reticle thickness, as shown in FIGS. 4A and 4C, a transmitted light leaks into the reflection field area, inducing a phenomenon in which an image of blurred edges of the transmission field stop, which is a reference pattern, is obtained. That is, the contrast deteriorates and the differential value (inclination) of the amount of light in the edges becomes smaller. Conversely, when there is no focal point shift, edges become vivid and the contrast, that is, the differential value (inclination) in edges of the amount of light takes a maximum value.

Thus, in the reticle defect inspection method according to the present embodiment, the second pulse motor 32, which is a focusing lens driving mechanism, is moved to pick up an image of the transmission field stop 22 by the third imaging sensor 58. Then, the picked-up image is input into the correcting mechanism 70 to calculate a differential value (inclination) of the amount of light in edges by an arithmetic processing part thereof. Then, the arithmetic processing part of the correcting mechanism 70 outputs information of the focusing lens position where the value takes the maximum value to the focusing lens driving mechanism. Based on the information of the focusing lens position, the focusing lens 28 is moved to correct a focal point shift.

According to the present embodiment described above, a reticle defect inspection apparatus and a reticle defect inspection method that can carry out a defect inspection with high detection sensitivity by correcting a focal point shift of a transmitted illumination light due to variations in reticle thickness with ease can be applied.

An embodiment of the present invention has been described above with reference to concrete examples. Though a description of components that are not directly needed for describing the present invention such as a reticle defect inspection apparatus and a reticle defect inspection method is omitted in descriptions of the embodiment, components needed for a reticle defect inspection apparatus or a reticle defect inspection method can suitably be selected and used.

In addition, all reticle defect inspection apparatuses and reticle defect inspection methods having components of the present invention and whose design can suitably be modified by a person skilled in the art are included in the scope of the present invention. Additional advantages and modification will readily occur to those skilled in the art.

Additional advantages and modification will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A reticle defect inspection apparatus for inspecting for defects on a sample using a pattern image obtained by irradiating the sample on which patterns are formed with light, comprising:
   a light source;
   an optical system of transmitted illumination configured to irradiate one surface of the sample with a first inspection light;
   an optical system of reflected illumination configured to irradiate another surface of the sample with a second inspection light;
   a detecting optical system configured to simultaneously detect a transmitted light obtained by the first inspection light being transmitted through the sample and a reflected light obtained by the second inspection light being reflected by the sample;
   a first imaging device configured to inspect the pattern image obtained by the transmitted light; and
   a second imaging device configured to inspect the pattern image obtained by the reflected light, wherein
   the optical system of transmitted illumination comprises a focusing lens being located on an optical path between the light source and the sample, and a focusing lens driving mechanism configured to correct a focal point shift of the transmitted light resulting from a thickness of the sample by moving the focusing lens.

2. The apparatus according to claim 1, further comprising:
   a reference pattern configured to correct a focal point shift of the transmitted light resulting from the thickness of the sample, the reference pattern being provided in the optical system of transmitted illumination, and the reference pattern being located on the optical path between the light source and the sample; and
   a third imaging device configured to observe an image of the reference pattern.

3. The apparatus according to claim 2, further comprising a correcting mechanism configured to make corrections using the focusing lens driving mechanism so that a maximum contrast of a reference pattern image obtained by imaging the reference pattern is achieved.

4. The apparatus according to claim 1, further comprising a correcting mechanism configured to correct a focal point shift of the transmitted light using thickness information of the sample, which is measured in advance, and the focusing lens driving mechanism.

* * * * *